Figure 1:
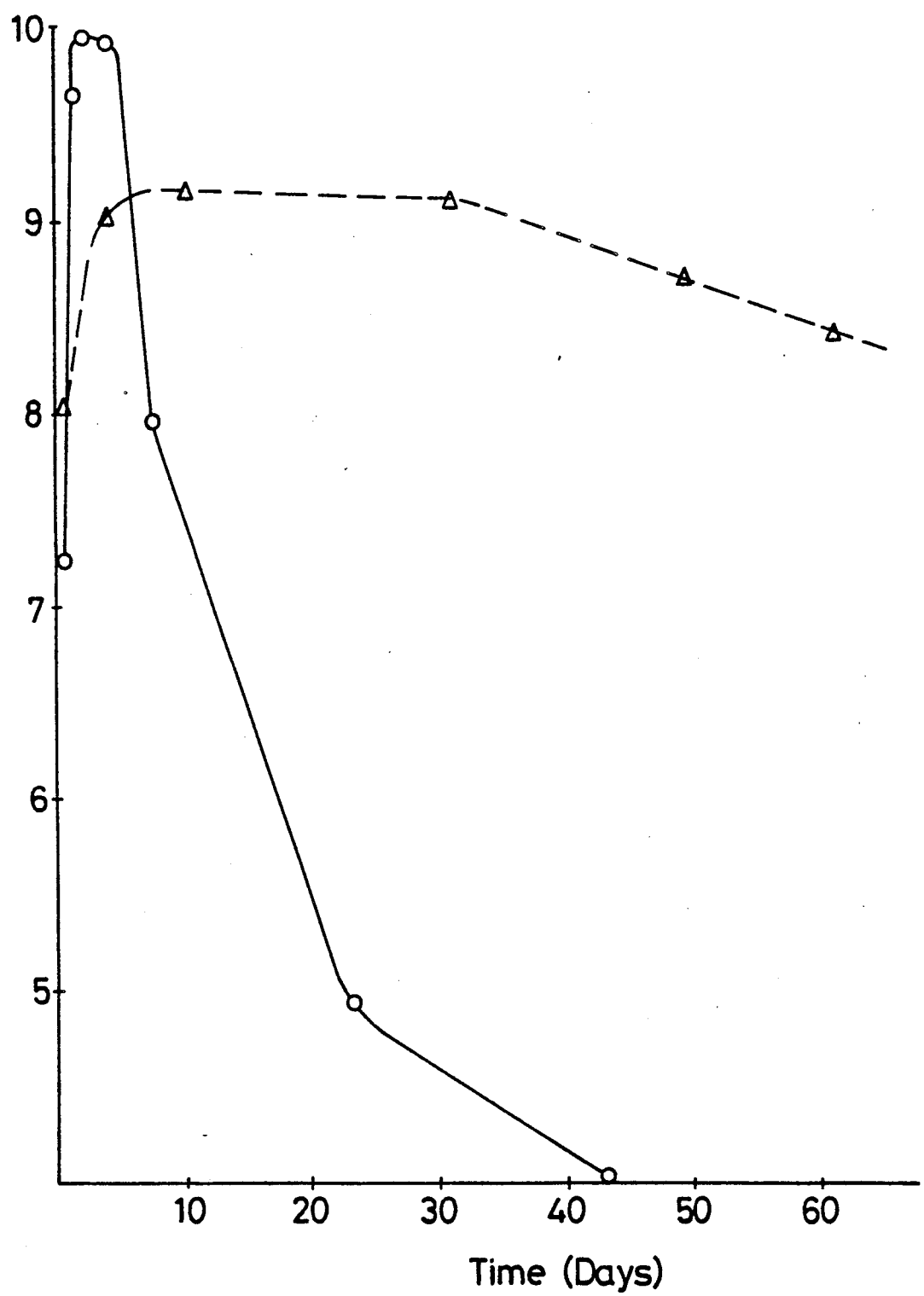
Figure 2:
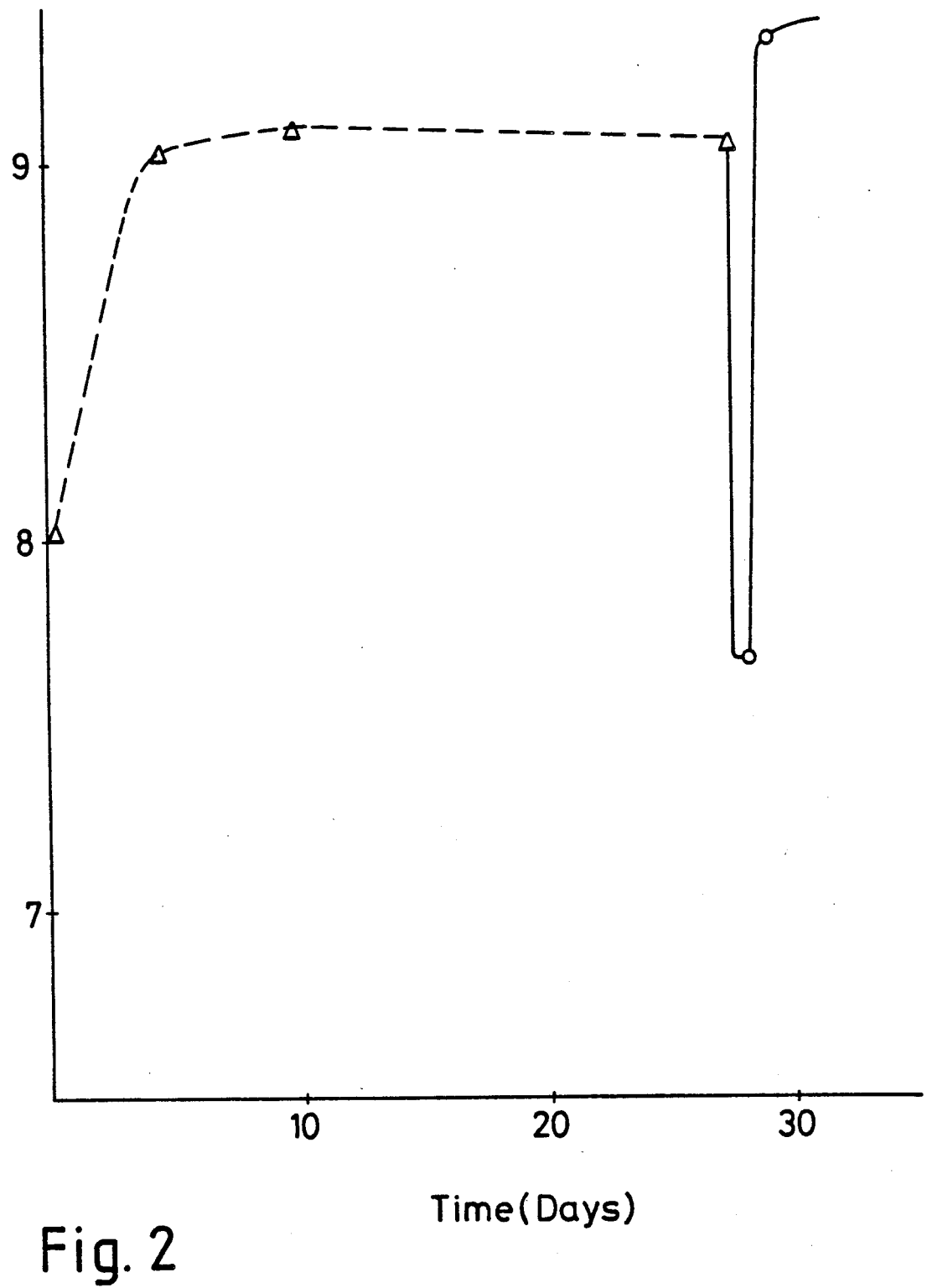

United States Patent [19]

Bryan-Jones

[11] Patent Number: 4,999,301

[45] Date of Patent: Mar. 12, 1991

[54] CULTURE AND PRESERVATION OF MICROORGANISMS WITHIN A CONCENTRATED MEDIUM

[75] Inventor: David G. Bryan-Jones, Stirling, Scotland

[73] Assignee: 501 United Distillers plc, Edinburgh, United Kingdom

[21] Appl. No.: 250,620

[22] PCT Filed: Dec. 30, 1987

[86] PCT No.: PCT/GB87/00926

§ 371 Date: Sep. 27, 1988

§ 102(e) Date: Sep. 27, 1988

[87] PCT Pub. No.: WO88/05076

PCT Pub. Date: Jul. 14, 1988

[30] Foreign Application Priority Data

Jan. 8, 1987 [GB] United Kingdom ............ 8700354

[51] Int. Cl.$^5$ .................. C12N 1/20; C12N 1/04; C12N 1/00

[52] U.S. Cl. .................. 435/252.5; 435/252.9; 435/253.6; 435/260; 435/839; 435/857

[58] Field of Search .............. 435/252.5, 252.9, 253.6, 435/260, 839, 857, 244, 245

[56] References Cited

FOREIGN PATENT DOCUMENTS 52-108079 9/1977 Japan .

OTHER PUBLICATIONS

Klaar, "Reproduction and Preservation of *Lactobacillus plantarum, Lactobacillus acidophilus* and *Propionibacterium shermanii* Cells in Concentrated Media," Eesti Pollumajanduse Akad. Tead. Toode Kogumik, 1967, No. 55, 125-42.

G. Bryan-Jones, "II.5 Lactic Acid Bacteria in Distillery Fermentations," in *Fourth Long Ashton Symposium 1973 Lactic Acid Bacteria in Beverages and Food*, proceedings of a Symposium held at Long Ashton Research Station University of Bristol, 19-21 Sep. 1973, Ed. Carr, J. G., Cutting, C. U. and Whiting, G. C., Academic Press, N. Y. (1975), pp. 165-175.

*Primary Examiner*—David M. Naff
*Assistant Examiner*—Eric J. Kraus
*Attorney, Agent, or Firm*—Mason, Fenwick & Lawrence

[57] ABSTRACT

Microorganisms are stored for long periods of time in storage mediums which preferably contain a sufficiently high concentration of nutrients and growth inhibiting substances to maintain microorganisms, such as bacteria, in the stationary or death phase of their growth cycle. Upon dilution of the growth medium, the concentration of the inhibiting substances is lowered below that inhibiting the growth of the microorganisms, while sufficient nutrients remain to allow for the number of microorganisms to rapidly increase. In a preferred embodiment, the growth medium contains between 10% and 30% solids which are the waste products of a food or fermentation process, and the microorganisms are *lactobacillus plantarum* or *bacillus subtilis*.

16 Claims, 2 Drawing Sheets

CULTURE AND PRESERVATION OF MICROORGANISMS WITHIN A CONCENTRATED MEDIUM

This invention relates to the culture of microorganisms. More particularly it relates to the preservation of viable microorganisms and a method of producing a quantity of such microorganisms for industrial use. A good example of this is the treatment of grass for ensilage.

Microorganisms are cultured in nutrient media typically composed of water, carbon sources, nitrogen sources and mineral salts, which provide for growth under favourable conditions of temperature, pressure, pH etc. In such a medium microorganisms proceed through a typical growth cycle, which is a consequence of the relative balance between the growth and death rates of the microorganisms, and which may be described as consisting of a lag phase or delayed growth phase, during which the microorganisms become acclimated to the environment of the nutrient medium; an exponential growth phase, during which numbers increase logarithmically with time; an apparently stationary phase, during which an equilibrium culture density is reached; and finally a phase of accelerating death. The stationary phase arises from a number of factors, such as the accumulation of toxic substances and the depletion of nutrients, which inhibit the growth of the microorganisms. The rate of growth decreases and the death of cells commences, the balance between cell growth and cell death determining the population of viable microorganisms. In their natural environment a slow rate of cell death can prolong the stationary phase of the growth cycle, so effecting a strategy for maintaining viability between the intermittent occurrence of nutrients. This prolonged stationary phase of the growth cycle is the natural condition of many non-spore forming microorganisms between short spells of active growth, when nutrients once again become available.

Microorganisms are useful industrially, for example, for cheese manufacture, silage fermentation, effluent treatment, and deposit removal. The present method of producing microorganisms for such use is to grow them under optimum conditions (using the optimum growth-/nutrient medium), harvest them, then preserve them by drying, freezing or freeze drying until ready for use. However all these methods of producing an industrially useful quantity of microorganisms are costly.

It is an object of the present invention to provide a means of preserving microorganisms in a viable condition without the need for drying and the like.

According to a first aspect of the invention there is provided a microorganism culture kit comprising a quantity of viable microorganisms, and a concentrated growth medium containing the microorganisms, the degree of concentration of the growth medium being such that the normal death phase is delayed and that on subsequent dilution of said growth medium, the number of microorganisms increase.

The length of the growth cycle of the microorganisms in the concentrated growth medium will increase with concentration. Generally, they will go through in sequence, a growth phase in which the rate of growth of the microorganisms is greater than the rate of death thereof, at the top end of this growth phase the number of microorganisms will be at a maximum; a stationary phase in which the growth and death rates are approximately equal; and a death phase in which the death rate of the microorganisms is greater than the growth rate thereof.

A microorganism culture in a medium designed for optimum growth of the microorganism will be taken as standard or normal.

As can be seen, whereas previous methods of supplying microorganisms all involve firstly growing the microorganisms in a normal/optimum growth medium, the present invention is contrary to this in that the growth medium purposely is not at optimum conditions: it is more concentrated.

The advantage of such a concentrated medium is that the shelf life of the microorganisms is sufficiently increased. That is, it has been found that under optimum growth conditions the limiting factor terminating the logarithmic growth phase is dominantly, depletion of one or more essential nutrients. In a concentrated medium, the normal logarithmic growth phase is more gradual but there is still a phase of growth. At the end of this growth phase, the growth is slowed down by a build up of inhibitors(such as by-products); but there is still an excess of nutrients present thereby allowing slow growth to continue and the high osmotic pressure and presence of insoluble solids appear to contribute towards retarding the death rate. The result is a prolonged stationary phase followed by a very gradual death phase. Therefore a significant proportion of the maximum number of microorganisms which were grown remain viable after a prolonged period.

The length of the growth cycle of the microorganisms will generally increase at the optimum growth medium is further concentrated. For commercial purposes alone the maximum concentration of the growth medium will be that which can still just pour. At the lower limit, there must be a suficient number of viable microorganisms on purchase thereof so that they can quickly by grown up to an industrially useful quantity. Such a lower limit is thought to be at least 0.5% of the maximum quantity remain viable after two months, preferably at least 1%, more preferably at least 5%, and most preferably at least 10% of the microorganisms remain viable after 2 months.

The optimum nutrient medium for any microrganism is a matter of general knowledge. It is found economical where possible, however, to use at least one waste or by-product from an industrial process in the growth medium. Preferably the waste products are comprised in a waste stream which can be concentrated or diluted as required. The waste products are preferably obtained from a food manufacturing process (such as would give whey waste) or a fermentation process. Spent wash or spent wash syrup (such as wheat spent wash) are particularly preferred for use with the growth medium, and are obtained as a byproduct from alcohol production, particularly in the manufacture of whisky.

These effluents contain proteinaceous material, amino acids, yeast residues and other assimilable materials which are available for use in the culture of microorganisms. Spent wash typically contains from 2% to 12% solids and spent wash syrup from 12% to 55% solids. The solids content in the concentrated medium is preferably between 10% and 30%, advantageously about 16%.

From this discussion it will be appreciated that use of an industrial waste product or stream as discussed above for a concentrated growth medium or a portion thereof, forms a second aspect of the invention.

It is important to limit as far as possible the growth of contaminant microorganisms or undesirable mutants. If the storage medium, however, resembles in as many parameters as possible the environment in which the microorganisms are ultimately to be used, then undesirable mutants are unlikely to outgrow other cells. Inhibitors could be added and/or pH chosen to selectively inhibit undesirable microorganisms. Propionic acid has been successfully used in some systems as an inhibitor.

The prolonged stationary phase is believed to be achieved by control of the rates of cell growth and cell death compared to a normal laboratory culture. Some slowing of the growth rate of the microorganisms is attributed to pH, osmotic pressure and the utilisation of available nutrients, but a relatively greater slowing of cell death rate is controlled by a number of factors including pH, osmotic pressure, the concentration of toxic substances, temperature, insoluble particles and the agglomeration of cells into clumps. A knowledge of the effect of these factors in prolonging the stationary phase is required to design a suitable concentrated medium for each particular microorganism of mixture of microorganisms.

It will be appreciated that not all microorganisms could be stored in a concentrated form of their optimum growth medium. For example some pathogenic microorganisms require very specific conditions for growth. It will, however, be apparent by trial and error which microorganisms could be so stored. There are a number of industrially useful microorganisms which could be so stored, especially such as *Lactobacillus plantarum* (for silage), and *Bacillus subtilis* (for effluent treatment).

As has been mentioned, a significant feature of the present invention is that the concentrated medium still contains an excess of essential nutrients well into the death phase. Thus, if the concentrated medium is diluted below the concentration inhibiting the microorganisms' growth, the microorganisms will start to increase in number again; to grow.

Therefore, in accordance with a third aspect of the present invention, a method of providing a viable quantity of microorganisms comprises taking a microorganism culture kit as defined in the first aspect of the invention and diluting the concentrated growth medium, where the microorganisms are in the stationary phase or death phase of their growth cycle, so that inhibitory substances are at a concentration below that inhibiting the microorganisms' growth.

The advantage of this method is that a sufficient number of the microorganisms will still be viable on sale of the culture kit, so that they can quickly and easily be grown up to a required, useful quantity. Moreover, this method of supplying a useful quantity of microorganisms is very economical. The growth of the microorganisms will depend on the dilution factor, which ultimately will be such as to provide a microorganism culture whose numbers are dominantly limited by depletion of one or more essential nutrients. In such a system, the optimum quantity of microorganisms will be produced.

From a commercial consideration, the dilution factor should be such as to obtain an industrially useful quantity of microorganisms in a short period, preferably less than three days, but most preferably up to two days. In practical terms an industrially useful quantity is preferably at least 60% of the maximum quantity which would be obtained in an optimum growth medium, and is more preferably at least 80%.

Further nutrients may need to be added on dilution of the growth medium. This, however, complicates the use of the culture kit and it is preferred, where possible, to concentrate the growth medium sufficiently at the start so that no further nutrients need be added.

The invention is illustrated in the following examples. Examples 1 to 4 are used to supply a quantity of microorganisms for silage treatment, whereas example 5 supplies a quantity of microorganisms for effluent treatment.

EXAMPLE 1

Two strains of *Lactobacillus plantarum* were first grown in MRS or other suitable medium. A 1% by volume inoculum was then added to a storage medium consisting of wheat spent wash syrup (a distillery by-product) at 16% dry matter, to which acetate/acetic acid buffer (pH 5.0, 0.2 Molar) and sucrose (0.05 Molar) have been added. This was held at ambient temperature (20° C. ±4° C.). After 7 days the bacteria had grown to $1 \times 10^9$ bacteria per milliliter. After a further 4 weeks the medium was diluted 10 fold and sucrose (final concentration 0.03 Molar) and acetate buffer (final concentration 0.02 Molar) added. The diluted medium was stored at ambient temperature for 48 hours, during which time the bacteria grew to $1 \times 10^9$ bacteria per milliliter.

EXAMPLE 2

Repeating steps of Example 1, the same inoculum was added to a similar medium as before, but containing acetate/acetic acid buffer, pH 5.0, 0.4 Molar and sucrose, 0.55 Molar. This was held at ambient temperature (20° C. ±4° C.). After 7 days the bacteria had grown to $2 \times 10^9$ bacteria per milliliter. After a further 4 weeks the medium was diluted 20 fold. The diluted medium was stored at ambient temperature for 48 hours, during which time the bacteria grew to $1 \times 10^9$ bacteria per milliliter.

EXAMPLE 3

Repeating steps of Example 1, the same inoculum was added to a similar medium as Example 2, except that propionic acid (10 parts per million) and hexanoic acid (10 parts per million) were further added. This was held at ambient temperature (20° C. ±4° C.). After 7 days the bacteria had grown to $2 \times 10^9$ bacteria per milliliter. After a further 4 weeks the medium was diluted 25 fold. The diluted medium was stored at ambient temperature for 48,hours during which time the bacteria grew to $1.0 \times 10^9$ bacteria per milliliter.

EXAMPLE 4

Repeating steps of Example 1, the same inoculum was added to a similar medium as Example 2, except that propionic acid (1000 parts per million) and calcium carbonate (0.2%) were further added. This was held at ambient temperature (20° C. ±4° C.). After 7 days the bacteria had grown to $2 \times 10^9$ bacteria per milliliter. After a further 4 weeks The medium was diluted 20 fold. The diluted medium was stored at 25° C. for 24 hours, during which time the bacteria grew to $1.5 \times 10^9$ bacteria per milliliter.

EXAMPLE 5

A strain of *Bacillus subtilis* is first grown in Nutrient Broth or other suitable medium. A 1% by volume inoculum was then added to a storage medium consisting of wheat spent wash syrup (a distillery by-product) at 16% Dry Matter adjusted to pH 6.8 with ammonium hydroxide, to which a lactose (0.56 Molar) and potassium dihydrogen orthophosphate (0.1 Molar) have been added. This was incubated with aeration at 30° C. for 24 hours and then held at ambient temperature (20° C. ±4° C.). After 7 days the bacteria had grown to $8 \times 10^8$ bacteria per milliliter. After a further 4 weeks the medium was diluted 10 fold. The diluted medium was incubated with aeration at 25° C. for 24 hours during which time the bacteria grew to $2 \times 10^9$ bacteria per milliliter.

A comparison of a culture *Lactobacillus plantarum* on an optimum growth medium (Oxoid) and a concentrated growth medium in accordance with the invention is illustrated in Graphs 1 and 2 of the drawings.

Graph 1 shows that the culture in the Oxoid medium has a growth cycle of about 40 days after which time there is about a 100% decrease from the maximum quantity of microorganisms. On the other hand, the viable culture in the concentrated nutient medium after 60 days is still about 1C % of the maximum (m). The useful shelf life is at least three months. Furthermore, if the Oxoid medium is diluted, there is no overall increase in the rate of growth of the microorganisms. Conversely, as illustrated by Graph 2, since only a small percentage of nutrients have been consumed, the microorganisms will grow normally if the concentrated medium is diluted. In this system dilution (25 times) to the optimum growth medium results in logarithmic growth of the microorganisms. The graph shows the Log no of bacteria per ml, thus the total quantity of bacteria actually produced is masked by the extra water.

The examples will now be examined and compared.

A comparison of examples 1 and 2, shows that the sucrose can be concentrated up to 0.55 Molar and therefore no further addition on dilution is required. The optimum pH is 5 (0.4M).

Example 4 shows that propionic acid increases the eventual quantity of microorganisms. This acid acts as an inhibitor for moulds, bu[is also thought to increase the growth rate. The calcium carbonate acts as a buffering agent.

The 16% DM obtained from the spent wash syrup is the optimum and maximum concentration which will still pour. The dilution factor for optimum growth is about 20 to 25, but it is still acceptable between a dilution factor of 5 and 100.

Example 5 shows the preferred conditions for providing *Bacillus subtilis* for effluent treatment.

As shown by the description and examples a particularly useful source of nutrients for the concentrated growth medium is that of industrial waste products. Therefore a second aspect f the invention provides for use of a by-product or waste product from a suitable industrial process for a concentrated growth medium or a portion thereof, particularly a food or fermentation process, more particularly a process for the production of alcohol, advantageously whisky manufacture.

The example in the graphs for the *Lactobacillus plantarum* system shows that at least 10% of the maximum amount of microorganisms are still viable after about 2 months. It is thought that the percentage viability could be raised for this system by, for example, storing the culture kit in a fridge. For other systems the percentage viability will vary, and could well be much more than 10% after 2 months.

I claim:

1. A method of providing bacteria for industrial use, comprising the step of:
    combining bacteria with a growth medium capable of delaying onset of the death phase of the growth cycle of said bacteria, wherein said growth medium comprises from about 10% to about 30% solids, and said bacteria are selected from the group comprising *Lactobacillus plantarum* and *Bacillus subtilis*; and
    diluting said growth medium containing said bacteria to increase the number of said bacteria.

2. A method according to claim 1, wherein: said dilution step dilutes said growth medium by about 5 to about 100 fold.

3. A method according to claim 1, wherein: prior to said dilution step, said growth medium comprises from about 16% to 30% solids, and said dilution step dilutes said growth medium by about 10 to about 25 fold.

4. A method according to claim 1, wherein: said growth medium further comprises a waste product from a food manufacturing process or an alcohol fermentation process.

5. A method according to claim 4, wherein: said waste product is spent wash syrup from the production of alcohol.

6. A method according to claim 1, wherein: said growth medium further comprises a buffer.

7. A method according to claim 6, wherein: said buffer is selected from the group comprising acetic acid/acetate, and carbonic acid/carbonate.

8. A method according to claim 7, wherein: said acetic/acetate buffer is about 0.2M to about 0.4M and has a pH of about 5.

9. A method of providing bacteria for industrial use, comprising the step of:
    combining bacteria with a growth medium capable of delaying the onset of the death phase of the growth cycle of said bacteria, wherein said growth medium comprises from about 10% to about 30% solids, and said bacteria are lactobacillus; and
    diluting said growth medium containing said bacteria to increase the number of said bacteria.

10. A bacterial culture kit, comprising:
    bacteria in a growth medium, said growth medium comprising from about 10% to about 30% solids to delay onset of the death phase of the growth cycle of said bacteria, said solids comprising waste products from a food manufacturing process or an alcohol fermentation process, and said bacteria being selected from the group comprising *bacillus subtilus* and *lactobacillus plantarum*.

11. A bacterial culture kit according to claim 10, wherein:
    at least 0.5% of the maximum number of said bacteria still remain viable after two months.

12. A bacterial culture kit according to claim 10, wherein:
    upon subsequent dilution of said growth medium, at least 60% of the potential maximum quantity of said bacteria are obtained in less than about three days.

13. A bacterial culture kit according to claim 10, wherein:

said waste product is spent wash syrup from the production of alcohol.

14. A bacterial culture kit according to claim 10, further comprising a buffer.

15. A bacterial culture kit according to claim 14, wherein:
said buffer comprises acetic acid and acetate.

16. A bacterial culture kit, comprising: bacteria in a growth medium, said growth medium comprising from about 10% to about 30% solids to delay the onset of the normal death phase of the growth cycle of said bacteria, said solids comprising waste products from a food manufacturing process or an alcohol fermentation process, and said bacteria are lactobacillus, wherein upon subsequent dilution of said growth medium, the number of said bacteria increases.

* * * * *